United States Patent [19]

Zimmermann

[11] Patent Number: 4,971,910

[45] Date of Patent: Nov. 20, 1990

[54] MAGNETIC DEVICE FOR THE FUSION OF CELLS

[75] Inventor: Ulrich Zimmermann, Hürtgenwald-Gey, Fed. Rep. of Germany

[73] Assignee: Kernforschungsanlage Julich, Julich, Fed. Rep. of Germany

[21] Appl. No.: 226,071

[22] Filed: Jul. 29, 1988

Related U.S. Application Data

[62] Division of Ser. No. 619,013, Jun. 11, 1984, Pat. No. 4,784,594.

[30] Foreign Application Priority Data

Jun. 11, 1983 [DE] Fed. Rep. of Germany ....... 3321238

[51] Int. Cl.$^5$ .................... C12M 1/42; C12N 15/02
[52] U.S. Cl. .................... 435/287; 435/803; 935/85; 935/88; 204/DIG. 5
[58] Field of Search .............. 435/173, 287, 284, 285, 435/286, 299, 803; 436/526, 806; 204/DIG. 5, 302, 299 R; 935/85, 88

[56] References Cited

U.S. PATENT DOCUMENTS

| 2,440,472 | 4/1948 | Horner et al. | 435/287 X |
|---|---|---|---|
| 2,955,076 | 10/1960 | Gossling | 435/287 X |
| 3,095,359 | 6/1963 | Heller | 435/287 X |
| 3,709,791 | 1/1973 | Lichtenstein | 435/311 X |
| 3,871,961 | 3/1975 | Gianessi | 435/287 X |
| 3,970,518 | 7/1976 | Giaever | 435/287 X |
| 3,981,776 | 9/1976 | Saxholm | 435/287 X |
| 4,157,323 | 6/1979 | Yen et al. | 436/526 X |
| 4,201,635 | 5/1980 | Muller | 204/DIG. 5 X |
| 4,374,199 | 2/1983 | Carter | 435/173 X |
| 4,438,068 | 3/1984 | Forrest | 436/526 X |
| 4,441,972 | 4/1984 | Pohl | 935/93 X |
| 4,469,759 | 9/1984 | Newill | 204/DIG. 5 X |
| 4,508,625 | 4/1985 | Graham | 435/173 X |
| 4,561,961 | 12/1985 | Hofmann | 204/308 X |
| 4,578,167 | 3/1986 | Schoner | 435/287 X |
| 4,578,168 | 3/1986 | Hofmann | 204/183.1 X |

OTHER PUBLICATIONS

Biological Abstracts, vol. 70, No. 5, (1980) abstract No. 31448, Stephenson et al.

Stephenson et al., American Journal Veterinary Research, vol. 41, No. 2, (1980), pp. 234–240.

Hurrell (editor), Monoclonal Hybridoma Antibodies: Techniques & Applications, CRC Press, Boca Raton, Florida, 1982, pp. 20–24.

Primary Examiner—Robert A. Wax
Assistant Examiner—William H. Beisner
Attorney, Agent, or Firm—Lorusso & Loud

[57] ABSTRACT

Disclosed is a process and device for fusing cells in which the cells are doped with magnetic particles and exposed to a nonhomogeneous magnetic field which permeates the fusion space in such a way that the doped cells collect close together, and then, in order to create the disruptions in the membrane structures of the adjacent cells, the cells are exposed either to the pulse of an electric field of at least the level of the breakdown voltage or to chemicals which cause the disruptions in the membrane structure such as polyethylene glycol, or to inactivated viruses which cause the disruptions in the membrane structure such as Sendai viruses.

6 Claims, 3 Drawing Sheets

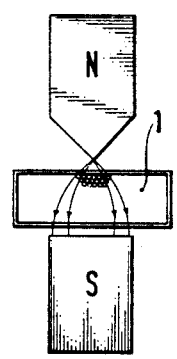
FIG. 1
FIG. 2
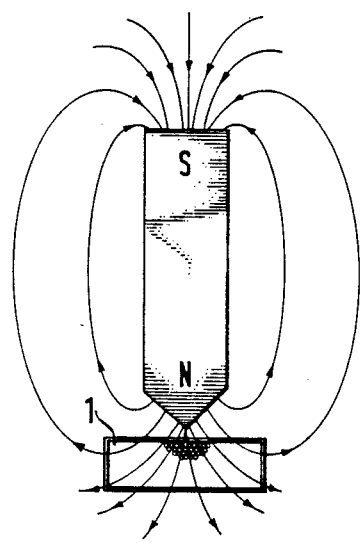

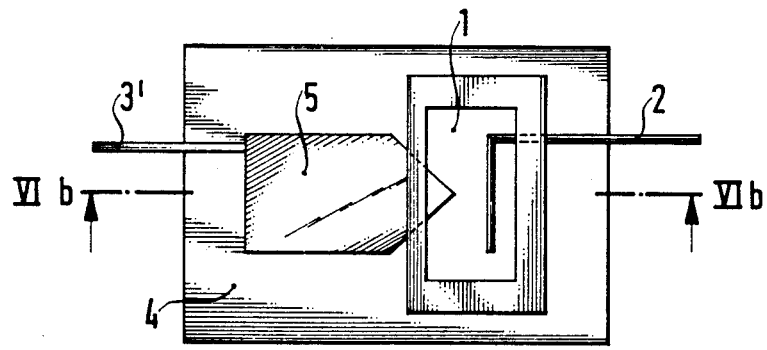
FIG. 6a
FIG. 6b
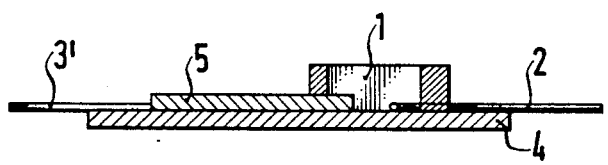

MAGNETIC DEVICE FOR THE FUSION OF CELLS

This is a divisional of co-pending application Ser. No. 619,013 filed on June 11, 1984 which application issued as U.S. Pat. No. 4,784,594 on Nov. 15, 1988.

BACKGROUND OF THE INVENTION

The invention pertains to a procedure for the fusing of cells in which the cells in a cell suspension in the fusion space are brought close together by external forces and disruptions are caused by external effects in the membrane structure of the adjacent cells; these disruptions lead to the formation of membrane bridges between adjacent cells and to the fusion of the cells.

If two cells in a suspension touch one another and close contact develops between the membranes of the two cells, they should fuse since the components in the membranes are mobile. Such spontaneous fusion of cells is observed extremely rarely or not at all under natural conditions. A known exception is the fertilization of an egg cell by a semen cell during sexual reproduction. Spontaneous fusion is hindered by the negative charge of the phospholipids and other membrane components. This negative charge causes the cells to repel once they have come to within a certain distance of one another. Cell fusion requires, however, that the two membranes be able to come within less than $10^{-7}$ cm.

The fusion of cells which is carried out by technical means can be used in a broad range of applications. Thus, for biomedical research it is of great interest to fuse a large number of cells. When the cells, which are created by fusing several or, if necessary, many cells (for example, 1,000 to 10,000 corpuscles), are of the appropriate size, microelectrodes micro pressure-measuring probes and other sensors can be introduced into the large cell without irreversibly destroying the membrane. The technique of directly recording a number of cells and membrane functions by means of the sensors is of importance to clinical diagnosis, for instance in the early detection of diseases as well as in general for basic research.

The cell fusion technique can also be used to form hybrid cells by fusing two cells of different origin. In this case cell hybrids can be formed from plant cells from which, in turn, whole plants can be cultivated or cell hybrids can be obtained from animal cells by means of which monoclonal antibodies, for instance, antibodies to tumors and leukemic cells, can be produced. As an example, let us mention the fusion of a lymphocyte cell with a myeloma cell, which is of great interest particularly to medicine and pharmacology. Certain lymphocytes form antibodies to foreign substances in the organism, for instance, to a foreign protein which has been injected into the blood stream. If the lymphocytes are isolated and fused with a tumor cell such as a myeloma cell, then there is the chance that a so-called hybridoma cell will form which will have the properties of both parent cells. This cell will produce antibodies which are specific only to the corresponding foreign substance (so-called monoclonal antibodies). The cell will not die and, in contrast to a normal differentiated cell such as the lymphocyte, it can be permanently reproduced in nutrient media.

A procedure for the fusion of the cells of the type mentioned in the introduction is known from Biochemica et Biophysica Acta, 694 (1982), 227–277 (Electric Field-Mediacted Fusion and Related Electrical Phenomena, U. Zimmerman. In the case of this known procedure (the course of which can be observed under a microscope), the membrane contact is generated between at least two cells by applying an alternating, slightly nonhomogeneous field. Because of polarization processes in the cell, the electric field creates dipoles which mutually attract if the cells come close to one another during their migration in the electrical field (so-called dielectrophoresis). After a row of cells has been formed, disruptions in the membrane structures between adjacent cells are triggered by an electric breakdown pulse (J. Membrane Biol. 67, 165–182 (1982), Electric Field-Induced Cell-to-Cell Fusion, U. Zimmermann and J. Vienken). According to previous model concepts, holes are created in the membrane contact zone of adjacent cells in the process which lead to a cytoplasmic continuum between the two cells and to the formation of lipid bridges between the membranes of the adjacent cells. The lipid molecules are no longer arranged in their original membrane. As soon as a bridge has formed, energy factors lead to rounding off of the formation which has developed and which consists of cells which are connected by means of the lipid bridges.

In the implementation of the known procedure for collecting cells by dielectrophoresis, however, it is necessary for the solution which holds the cells during the execution of the procedure to be as non-conductive as possible, otherwise the generation of heat will be excessive, and this will lead to turbulences and disruption of the close menbrane contact between adjacent cells. This is disadvantageous to the extent that the cells have little or no tolerance for a solution which is only slightly conductive and therefore the cells can suffer damage in a medium of low conductivity, and this impairs, among other things, their longevity.

A way is also known of using certain chemicals such as polyethylene glycol (PEG) or inactivated viruses to eliminate the electrical repelling forces which occur when there is a short distance between the membranes of two cells. Both viruses and PEG interlace the two cell membranes so that close membrane contact is created. At the same time, the viruses and PEG create disruptions in the membrane structure which can be reinforced by establishing non-physiological conditions such as adding high concentrations of calcium ions and selecting a very high or low pH value. The effect of these disruptions is that holes form in the membrane contact zone and this leads to the formation of phospholipid bridges between the adjacent cell membranes. This leads to the fusion of the two cells, forming a new unit.

In the implementation of the known procedures mentioned above, however, the number of cells to be fused cannot be controlled. On the one hand, an excessively low cell density in the solution containing the cells leads in practice to no fusion products since the cells do not come into contact with one another. On the other hand, a cell density which is sufficient to achieve fusion (and which can also be achieved by centrifuging the solution containing the cells) in an uncontrolled fashion leads to products which consist of doubles, triples, quadruples or multiples of individual cells.

In particular with regard to the formation of hybrid cells by fusing only two cells of different origin, the above-mentioned known procedures are very unsatisfactory. The reason is that cell hybrids which feature a new combination of properties must be isolated through the use of very time-consuming selection methods after the known procedures are implemented. The production of cell hybrids from plant cells from which, in turn, whole plants can be cultivated or of cell hybrids from animal cells by means of which monoclonal antibodies, for instance to tumors and leukemia can be obtained, requires a fusion technique in which only two cells are fused at a time.

It is therefore a principal object of the present invention to create a procedure for fusing cells during which the cells can be in a more conductive solution but the cells are still initially brought close together by the actual procedural step of the fusion itself.

SUMMARY OF THE INVENTION

In accordance with the invention, this object is accomplished by providing a process and a device in which the cells are doped with magnetic particles and exposed to a heterogeneous magnetic field which permeates the fusion space in such a way that the doped cells collect close together, and then, in order to create the disruptions in the membrane structures of the adjacent cells, the cells are exposed either to the pulse of an electric field of at least the level of the breakdown voltage or to chemicals which cause the disruptions in the membrane structure such as polyethylene glycol, or to inactivated viruses which cause the disruptions in the membrane structure such as Sendai viruses.

BRIEF DESCRIPTION OF THE DRAWINGS

Practical versions of the device of the present invention are shown schematically in the drawings and are explained below in greater detail:

FIG. 1 shows the chamber space to receive the cell suspension with magnetic poles placed on both sides of the space, FIG. 2 shows the chamber space with a magnet placed on only one side of the space.

FIG. 6a shows a top view of the chamber to treat the cells in an electrical field with the pole shoe of the magnet which protrudes into the chamber space, FIG. 6b shows a longitudinal section to the chamber as shown in FIG. 6a along line A-B.

DETAILED DESCRIPTION OF THE PREFERRED EMBODIMENT

Figure 3:
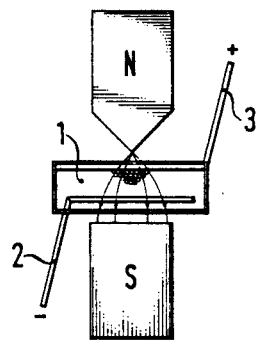
FIG. 3 shows the arrangement of the magnet in accordance with FIG. 1 with the electrodes protruding into the chamber space.

In the process and device of the present invention, cells are doped with magnetic particles and exposed to a heterogeneous magnetic field which permeates the fusion space in such a way that the doped cells collect close together, and then, in order to create the disruptions in the membrane structures of the adjacent cells, the cells are exposed either to the pulse of an electric field of at least the level of the breakdown voltage or to chemicals which cause the disruptions in the membrane structure such as polyethylene glycol, or to inactivated viruses which cause the disruptions in the membrane structure such as Sendai viruses.

The procedural step of the collection of the cells proceeds without any heat generation since it takes place under the action of magnetic forces only and without any electric current flowing. In this process the cells can be suspended even in a solution of considerable conductivity, for instance in the nutrient medium provided for the cells or in a medium, the potassium concentration of which is equal to the ion concentration of the cell. For the case where the fusion of the cells is to take place by electrical breakdown, because of the higher conductivity of the cell suspension a pulse length in the nanosecond range is sufficient.

With the procedure as described by the invention, controlled fusion of two or a predetermined number of cells is possible even if polyethylene glycol or Sendai viruses are used to disrupt the membrane structure. The number of cells to be fused in this case can also be controlled by the predetermined cell density in the cell suspension. In addition, with the procedure as described by the invention it is also possible to study in greater detail or optimize these "non-electrical" fusion procedures with regard to the doping of the agents which cause the disruptions. This is particularly true because the collection of the cells at the point of highest field density during the execution of the procedure as described by the invention can be observed under a microscope.

It is a good idea for the magnetic particles to be placed on the surfaces of the cells. In order to place the magnetic particles on the surfaces of the cells in as fine a distribution as possible and also to avoid having individual magnetic particles in the cell suspension which are not adsorbed on the cell surfaces, it is a good idea for the cells which are to receive the magnetic particles on their surfaces to be put in a solution which contains the magnetic particles dissolved colloidally. After a certain time after which the adsorption process has largely been completed, the excess magnetic particles present in the colloidal solution can be separated from them by centrifuging the cells off.

It may also be a good idea for the magnetic particles not to be adsorbed on the cell surfaces, but rather to be introduced into them. For this purpose the permeability of the membranes of the cells which are in a solution containing the magnetic particles in colloidal form is increased by applying an electric field pulse so that the magnetic particles can reach the inside of the cells. Thus, for example, a field pulse of approximately 15 kV/cm and a length of 50μsec is applied to a cell suspension which contains erythrocytes and $Fe_3O_4$ particles and thus the permeability of the cell membranes is increased enough to allow the $Fe_3O_4$ particles to enter the erythrocytes. After the healing of the increase in permeability, the magnetic particles which are additionally adsorbed at the surface can be removed by washing the cells several times with an isotonic solution.

It is a good idea to use ferromagnetic particles, in particular $Fe_3O_4$ particles as the magnetic particles.

For the case where a special orientation of the cells, in particular the lining-up of the cells in the form of a string of pearls, is desired, after collecting in the area of the highest field density of the magnetic field, the cells are briefly (generally for a few seconds) exposed to an external heterogeneous electrical field with a frequency of from 5 kHz to 2 MHz and an intensity of from 10 V/cm to 2000 V/cm, depending on the size of the cells, in such a way that the cells line up in the predetermined orientation. Since before the alternating electrical field is applied the cells have already been collected by the action of the magnetic field, it takes only a brief activation of the electrical field to achieve the desired concatenation of the cells. Heating of the cell suspension and thus of the cells is therefore largely avoided, while a row of cells is simultaneously produced.

For the case where the disruptions in the membrane structure are to be created through the use of polyethylene glycol or Sendai viruses, it is a good idea first to add the agent to the suspension containing the cells, then for the cells to collect and subsequently to be oriented in rows, and then to add calcium ions to cause the disruptions in the cell membranes. When Sendai viruses are used, the temperature is also raised to 37°C. With this procedure the effect of the agents takes hold only after the cells are oriented.

The implementation of the procedure as described by the invention using chemicals or viruses which cause the disruptions in the membrane structure calls for the use of a device in which a chamber is provided with a space composed of non-electroconductive walls to receive a cell suspension and in which a magnet is placed at the chamber in such a way that the volume of the chamber is permeated by a heterogeneous magnetic field. The magnet can be a permanent magnet, but it is also possible to use an electromagnet or a combination of the two with which it is possible to vary the magnetic field forces to, for example, virtually zero.

In order to carry out the practical versions of the procedure as described by the invention in which the disruptions in the cell membrane structures are caused by electrical breakdown, it is suitable to use a device in which a chamber is provided with space composed of non-electroconductive walls to receive a cell suspension; into this chamber there protrude at least three electrodes in such a way that an area bounded by the electrodes is formed in which the cells are exposed to an electrical field which is formed between the electrodes and in which a magnet is placed at the chamber in such a way that the space of the chamber is permeated by a heterogeneous magnetic field.

In the case of both versions of the device, an advantageous practical implementation of the device consists of having the magnet placed at the chamber in such a way that the magnetic field permeating the space originates with its maximum density at a part of the magnet which protrudes into the space of the chamber. The part of the magnet protruding into the chamber should in this case be a pole shoe which features a point or edge. In this case the pole shoe can also be one of the electrodes.

The arrangements shown in FIGS. 1 and 2 are used to implement those versions of the procedure in which the breakdown of the cells is caused by chemicals or inactivated viruses. Chamber space 1 in this case is either open or closed at the top; in the latter case it is possible to fill the chamber space with a cell suspension, for instance with feed and drain lines.

In the case of the arrangement shown in FIG. 3, two electrodes 2 and 3 protrude into the chamber space, the gap between which generally lies between 5 $\mu$m and 1,000 $\mu$m depending on the type and size of the cells to be treated. Electrode 3 which faces the north pole of the magnet and from which the magnetic field develops with a higher field density lies directly at the north pole of the chamber wall facing the north pole or is designed as this wall. To this electrode 3 come the cells which move towards the point of the greatest magnetic field density. In this case the cells collect densely packed together and can be fused by an electrical pulse equal to the breakdown voltage which is conducted via the electrodes. In this case the electrodes are generally connected to a (not shown in the drawing) device to generate a rectangular pulse (for the electrical breakdown) of up to 300 V.

If the cells are lined up in the form of a string of pearls after collecting in the magnetic field and before fusing, then in general a device to generate an alternating electrical field with an output voltage of 50 V is connected to the electrodes.

Figure 4:
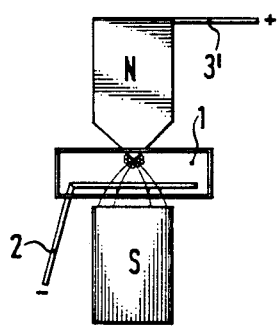
FIG. 4 shows the arrangement of the magnet in accordance with FIG. 1 with the part of the magnet which protrudes into the chamber space and which is designed at the same time as an electrode.

In the case of the device shown in FIG. 4, a part of the magnet (a pole shoe which features a point) protrudes into chamber space 1 and is simultaneously designed as electrode 3. In the case of this practical implementation, the cells collect directly at the point of electrode 3.

Figure 5:
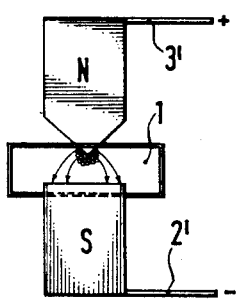
FIG. 5 shows the arrangement of the magnet in accordance with FIG. 1 in which both poles of the magnet protrude into the chamber space and are designed as electrodes.

A practical implementation of the device in which both the north and south poles of the magnet protrude into chamber space 1 and are simultaneously designed as electrodes 2 and 3 is shown in FIG. 5.

FIGS. 6a and 6b show a special practical implementation of a chamber for the electric treatment of the cells. Space 1 of the chamber is bounded by a base plate 4 and a side part 5 which forms the sidewalls of the space. A cover plate or foil can be used to provide the upper limit of the space.

Two electrodes 2 and 3 protrude into space 1 from which electrode 3 is designed in the shape of a plate and are made of a material with a relatively high magnetic permeability (soft iron). To implement the procedure in accordance with the invention, electrode 3 conducts the magnetic flux (for example, by making contact with a bar magnet) in order to achieve the desired variation of the magnetic lines of force which permeate space 1.

EXAMPLE 1

$Fe_3O_4$ particles (magnetite) were adsorbed at the surfaces of erythroleukemic cells (Friend cells). For this purpose 1 ml of the cell suspension was mixed with 100 l of a colloidal isotonic $Fe_3O_4$ solution. In order to increase the adsorption of the $Fe_3O_4$ particles, 1 mg of pronase (or dispase) was also added (the colloidal $Fe_3O_4$ solution had been produced by filtering a $Fe_3O_4$ slurry through a membrane filter with a pore diameter of 0.45 $\mu$m). After an incubation time of approximately 1 hour after which the adsorption process had largely been completed, the cells were removed by centrifuging the excess $Fe_3O_4$ particles out of the solution since the $Fe_3O_4$ particles cannot be centrifuged off in the colloidal solution.

The cells which were doped with the magnetic particles were incubated in an isotonic 0.3 molar mannitol solution to which 41.5% polyethylene glycol (PEG; MW 6000) as well as 15% dimethlsulfoxide (DMSO) were added.

The cells were placed in a fusion chamber of the type shown in FIG. 1. The magnetic field strength of the magnet used at this surface was approximately 1 kG. (As it turned out, however, the collection process was noted even when a piece of magnetized sheet steel was used with erythrocytes which had been doped with $Fe_3O_4$ particles).

After the cells collected at the point of maximum field density, a solution which contained 10 mM of $CaCl_2$ in a 0.3 molar mannitol solution was carefully added to the chamber space. The addition of the calcium ions triggered the fusion of the adjacent cells by PEG.

EXAMPLE 2

As in example 1, Avena Sativa protoplasts were doped with magnetite particles and fused with PEG.

EXAMPLE 3

As described in example 1, erythroleukemic cells were doped with magnetite particles and collected in a magnetic field. The solution containing the cells, however, did not contain any PEG, but rather inactivated Sendai viruses in a concentration of approximately b $2 \times 10^3$ HAU/ml (hemagglutinating units). After the cells collected in the magnetic field, twice as much of a solution was added which contained approximately 4 mM/l of $CaCl_2$ in a phosphate-buffered isotonic NaCl solution. Subsequently raising the temperature to 37°C. triggered fusion.

EXAMPLE 4

As described in example 1, Avena sativa protoplasts were doped with magnetite particles and collected in a magnetic field. The suspension solution contained 5 mM of $CaCl_2$ and 1 mg of pronase/ml, which corresponds to an electric conductivity of $1 \times 10^{-3} \, \Omega^{-1} \times cm$. After the cells collected, a field pulse of 2400 V/cm with a length of 500 nsec was applied, and in this way the cells were fused.

EXAMPLE 5

As described in example 1, Avena sativa protoplasts were doped with magnetite particles and collected in a magnetic field. The suspension solution had the composition indicated in example 4. To form the rows of cells, an alternating electrical field with a frequency of 1500 kHz and an intensity of 200 V/cm was applied for 5 seconds. Then, as described in example 4, the cells were fused by means of an electric field pulse.

All of the above-indicated practical examples were implemented with the sort of chamber of the type shown in FIG. 6a/6b; in this case, however, no electric voltage was applied in examples 1-3.

The foregoing invention has been described with reference to its preferred embodiments. Although variations and modifications will occur to those skilled in the art, it is intended that such variations and modifications fall within the scope of the appended claims.

What is claimed is:

1. A device for use in fusing cells by creating disruptions in membrane structures of adjacent cells through the use of chemicals or viruses which lead to the formation of membrane bridges in adjacent cells, comprising:
    a chamber providing a space and composed of non-electroconductive walls which receives a cell suspension, and
    a magnet which is placed at the chamber in such a way that exactly one pole of the magnet having a point or edge protrudes into the space of the chamber and the space in the chamber is permeated by a nonhomogeneous magnetic field which has its highest density at the pole of the magnet which protrudes into the space of the chamber in order to draw cells close together when cells are in the chamber and doped with magnetic particles thereby facilitating the formation of membrane bridges in adjacent cells.

2. Device in accordance with claim 1 wherein the magnet is a permanent magnet or an electromagnet.

3. Device in accordance with claim 1 wherein the magnet consists of a combination of a permanent magnet and an electromagnet.

4. A device for use in fusing cells by creating disruptions in membrane structures of adjacent cells through the use of electrical fields which cause the formation of membrane bridges in adjacent cells, comprising,
    a chamber providing a space and composed of non-electroconductive walls which receives a cell-suspension into which at least two electrodes protrude in such a way that a region between the electrodes is formed in which the cells are exposed to an electrical field formed between the electrodes;
    wherein at least one of the at least two electrodes is a magnet which is placed at the chamber in such a way that exactly one pole of the magnet having a point or edge protrudes into the space of the chamber and the chamber is permeated by a nonhomogeneous magnetic field which has its highest density at the pole of the magnet which protrudes into the space of the chamber in order to draw cells close together when cells are in the chamber and doped with magnetic particles thereby facilitating the formation of membrane bridges in adjacent cells.

5. Device in accordance with claim 4 wherein the magnet is a permanent magnet or an electromagnet.

6. Device in accordance with claim 4 wherein the magnet consists of a combination of a permanent magnet and an electromagnet.

* * * * *